US00PP23606P3

(12) United States Plant Patent
Zaiger et al.

(10) Patent No.: US PP23,606 P3
(45) Date of Patent: May 21, 2013

(54) INTERSPECIFIC TREE NAMED 'BLACK SATIN'

(50) Latin Name: **Interspecific *Prunus* species**
Varietal Denomination: Black Satin

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 367 days.

(21) Appl. No.: 12/928,504

(22) Filed: Dec. 14, 2010

(65) Prior Publication Data

US 2012/0151640 P1 Jun. 14, 2012

(51) Int. Cl.
*A01H 5/00* (2006.01)

(52) U.S. Cl.
USPC ..... Plt./180

(58) Field of Classification Search ..... Plt./180
See application file for complete search history.

*Primary Examiner* — Kent L Bell

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with attractive dark red skin color.
2. Fruit with very good flavor and eating quality.
3. Regular and productive bearer of medium to large size fruit.
4. Relatively uniform size and maturity of fruit throughout the tree.
5. Fruit with good storage and shelf life.

1 Drawing Sheet

Botanical classification: Interspecific *Prunus* species.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of interspecific trees, which are known to us, and mentioned herein, 'Bella Royale' Interspecific (U.S. Plant Pat. No. 19,925) and our proprietary interspecific tree with the identification number '263LV260'.

STATEMENT REGARDING FEDERALLY SPONSORED RESEARCH AND DEVELOPMENT

Not applicable.

ORIGIN OF THE VARIETY

The new and distinct variety of interspecific tree, [*Prunus salicina*×(*Prunus salicina*×*Prunus armeniaca*)] was developed by us in our experimental orchard located near Modesto, Calif. as a selected seedling from open pollinated seed of our interspecific proprietary seedling with the field identification number '263LV260'. The seed parent (263LV260) originated as an open pollinated seedling selection from seed of 'Bella Royale' Interspecific (U.S. Plant Pat. No. 19,925). A large number of these open pollinated seedlings, growing on their own root system, were budded to older trees of 'Nemaguard' Rootstock (non-patented) to induce earlier maturity and fruit evaluation. Under close and careful observation the present seedling exhibited desirable tree and fruit characteristics and was selected in 2005 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree [Plum×Plum Cot] is of large size, vigorous upright growth and a regular bearer of large size fruit with very good flavor and eating quality. The fruit is further characterized by having a very dark red skin color, firm flesh that has a good balance between acid and sugar and being relatively uniform in size and maturity throughout the tree. In comparison to its seed parent '263LV260' the fruit is larger in size and is approximately 24 days later in maturity. In comparison to its ancestor 'Bella Royale' Interspecific (U.S. Plant Pat. No. 19,925) the fruit has darker red skin color and is approximately 10 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large, pruned to 3 to 3.5 meters in height and width for economical harvesting of fruit. Varies with different types of soil and cultural practices.

*Vigor.*—Vigorous, tree growth of approximately 1.5 to 2 meters the first growing season, varies with cultural practices, soil type, fertility and climatic conditions.

*Form.*—Upright, usually pruned to vase shape.

*Branching habit.*—Upright, crotch angle approximately 40°, increases with heavy crop load.

*Productivity.*—Productive, thinning and spacing of fruit necessary for desired market size fruit.

*Bearer.*—Regular, adequate fruit set 3 consecutive years. No alternate bearing observed.

*Fertility.*—Self sterile, pollinator required.

*Density.*—Medium dense, usually pruned to vase shape to increase sunlight to center of tree to enhance health of fruit spurs.

*Hardiness.*—Hardy in all stone fruit growing areas of California. Tree grown in USDA Hardiness Zone 9. Winter chilling requirement approximately 850 hours at or below 45° F.

Trunk:

*Size.*—Medium, 33.1 cm at 38 cm above ground level on a 5 year old tree.

*Stocky.*—Medium.

*Texture.*—Medium shaggy, roughness increases with age.

*Color.*—Varies from 10YR 2/2 to 10YR 4/2.

Branches:

*Size.*—Medium. Average circumference 16.1 cm at 1.2 meters above ground on a 5 year old tree. Crotch angle approximately 40°, increases with heavy crop load.

*Surface texture.*—New growth relatively smooth. Mature growth medium rough, roughness increases with age.

*Lenticels.*—Size — medium. Average length 3.0 mm. Average width 1.3 mm. Average number of 28 in a 25.8 sq cm surface of branch. Color varies from 10YR 4/8 to 2.5Y 6/10.

*Color.*—New growth varies from 2.5GY 5/8 to 5GY 6/6. Old growth varies from 7.5YR 3/4 to 10YR 3/4, varies with age of growth.

Leaves:

*Size.*—Small to medium. Average length 66.7 mm. Average width 24.1 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 20.6 mm. Average width 1.6 mm. Longitudinally grooved. Surface — pubescent, very short in length. Color varies from 5GY 4/8 to 5GY 6/6.

*Glands.*—Type — globose. Size — small. Average length 0.9 mm. Average diameter 0.4 mm. Number varies from 0 to 4, average number 2. Located primarily on the upper portion of the petiole and on the base of the leaf blade. Color varies from 2.5GY 6/10 to 2.5GY 5/6.

*Stipules.*—Average number 2 at the base of the petiole. Average length 4.5 mm. Margin — doubly serrulate. Color varies from 10Y 6/4 to 10Y 6/6.

*Color.*—Upper surface varies from 7.5GY 3/4 to 5GY 3/4. Lower surface varies from 5GY 4/4 to 5GY 5/6. Midvein color varies from 5GY 6/4 to 5GY 7/4.

Flower buds:

*Size.*—Small to medium. Average length 8.8 mm. Average diameter 4.1 mm.

*Hardiness.*—Hardy with respect to California winters.

*Form.*—Conical, becomes elongated just before opening.

*Pedicel.*—Average length 5.7 mm. Average width 0.7 mm. Color varies from 2.5GY 7/8 to 5GY 7/6. Surface — glabrous.

*Color.*—N 9.5/(white).

*Number of buds per spur.*—Average number 10, varies from 6 to 13.

Flowers:

*Blooming period.*—Date of First Bloom Feb. 27, 2010. Date of Petal Fall Mar. 10, 2010, varies slightly with climatic conditions.

*Size.*—Small to medium. Average height 12.1 mm. Average diameter 20.1 mm.

*Petals.*—Size — small to medium. Normally 5, alternately arranged to the sepals. Average length 10.7 mm. Average width 8.6 mm. Form — orbicular, narrows at point of attachment. Margin — entire. Color — N 9.5/(white). Both surfaces glabrous.

*Sepals.*—Number — normally 5, alternately arranged to petals. Size — small. Average length 3.1 mm. Average width 2.7 mm. Form — ovate, apex rounded. Margin — entire. Color — upper surface varies from 5GY 6/6 to 5GY 5/6. Lower surface varies from 5GY 5/6 to 5GY 6/6. Both surfaces glabrous.

*Stamens.*—Average number per flower 29. Average filament length 9.1 mm. Filament color N 9.5/(white). Anther color varies from 5Y 8/8 to 5Y 8/10.

*Pollen.*—Self sterile, pollinator required. Color varies from 5Y 8/6 to 5Y 8.5/8.

*Pistil.*—Normally 1. Surface pubescent. Average length 9.7 mm. Stigma height approximately 0.5 mm above anthers. Color varies from 10Y 8/6 to 2.5GY 8/6.

*Fragrance.*—Moderate to heavy aroma.

*Color.*—N 9.5/(white).

*Number flowers per flower bud.*—Average number 2, varies from 1 to 4.

*Pedicel.*—Average length 8.2 mm. Average width 0.7 mm. Color varies from 2.5GY 6/8 to 2.5GY 5/8. Surface — glabrous.

Fruit:

*Maturity when described.*—Firm ripe.

*Date of first picking.*—Aug. 11, 2010.

*Date of last picking.*—Aug. 18, 2010, varies slightly with climatic conditions.

*Size.*—Medium to large. Average diameter axially 56.6 mm. Average transversely in suture plane 57.7 mm. Average weight 115.6 grams, varies slightly with fertility of the soil, amount of thinning and climatic conditions.

*Form.*—Globose.

*Suture.*—Very slightly lipped, extends from base to apex.

*Ventral surface.*—Very slightly lipped.

*Apex.*—Rounded, some fruit with very slight tip.

*Base.*—Varies from flat to slightly retuse.

*Stem cavity.*—Rounded to slightly elongated in suture plane. Average depth 5.5 mm. Average diameter 7.2 mm.

Stem:

*Size.*—Small. Average length 10.3 mm. Average diameter 2.0 mm.

*Color.*—Varies from 10Y 6/8 to 7.5YR 3/4.

Flesh:

*Ripens.*—Evenly.

*Texture.*—Firm, meaty.

*Fibers.*—Few, small, tender.

*Firmness.*—Firm, similar to firmness of 'Bella Royale' Interspecific (U.S. Plant Pat. No. 19,925).

*Aroma.*—Moderate to heavy.

*Amydgalin.*—Undetected.

*Eating quality.*—Very good.

*Flavor.*—Very good, good balance between acid and sugar.

*Juice.*—Moderate to heavy amount, enhances flavor.

*Brix.*—Average 18.0°, varies slightly with amount of fruit per tree and climatic conditions.

*Color.*—Varies from 5Y 8/8 to 10R 6/8 next to skin. Pit cavity color varies from 10YR 8/8 to 10YR 7/8.

*Pit cavity.*—Average length 26.8 mm. Average width 17.2 mm. Average depth 5.4 mm.

Skin:

*Thickness.*—Medium.

*Surface.*—Nearly smooth.

*Pubescence.*—Moderate amount, very short.

*Tendency to crack.*—None.

*Color.*—Ground color varies from 2.5Y 8.5/8 to 5Y 8/8. Overspread with 5R 2/2 to 7.5R 3/10.

*Tenacity.*—Tenacious to flesh.

*Astringency.*—None.

Stone:

*Type.*—Clingstone.

*Size.*—Medium. Average length 25.5 mm. Average width 16.4 mm. Average thickness 9.6 mm.

*Form.*—Ovoid.

*Base.*—Usually flat, varies from flat to slightly rounded.

*Apex.*—Slightly pointed. Average length 1.6 mm.

*Surface.*—Slightly pitted throughout. A small narrow groove on each side of the suture plane.

*Sides.*—Unequal, one side extending slightly further from the suture plane.

*Ridges.*—A small narrow ridge on each side of the suture.

*Tendency to split.*—None.

*Color.*—Varies from 10YR 6/8 to 10YR 6/6 when dry.

Kernel:

*Size.*—Medium. Average length 14.9 mm. Average width 8.9 mm. Average depth 5.6 mm.

*Form.*—Ovate.

*Viability.*—Viable, complete embryo development.

*Skin color.*—Varies from 5Y 8.5/6 to 5Y 8/6.

Use: Dessert.

*Market.*—Local and long distance.

Keeping quality: Good, held firm in cold storage 3 weeks at 38° to 42° F. without shriveling, internal breakdown of flesh or appreciable loss of eating quality.

Shipping quality: Good, showed minimal skin scarring or bruising during picking, packing or shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described.

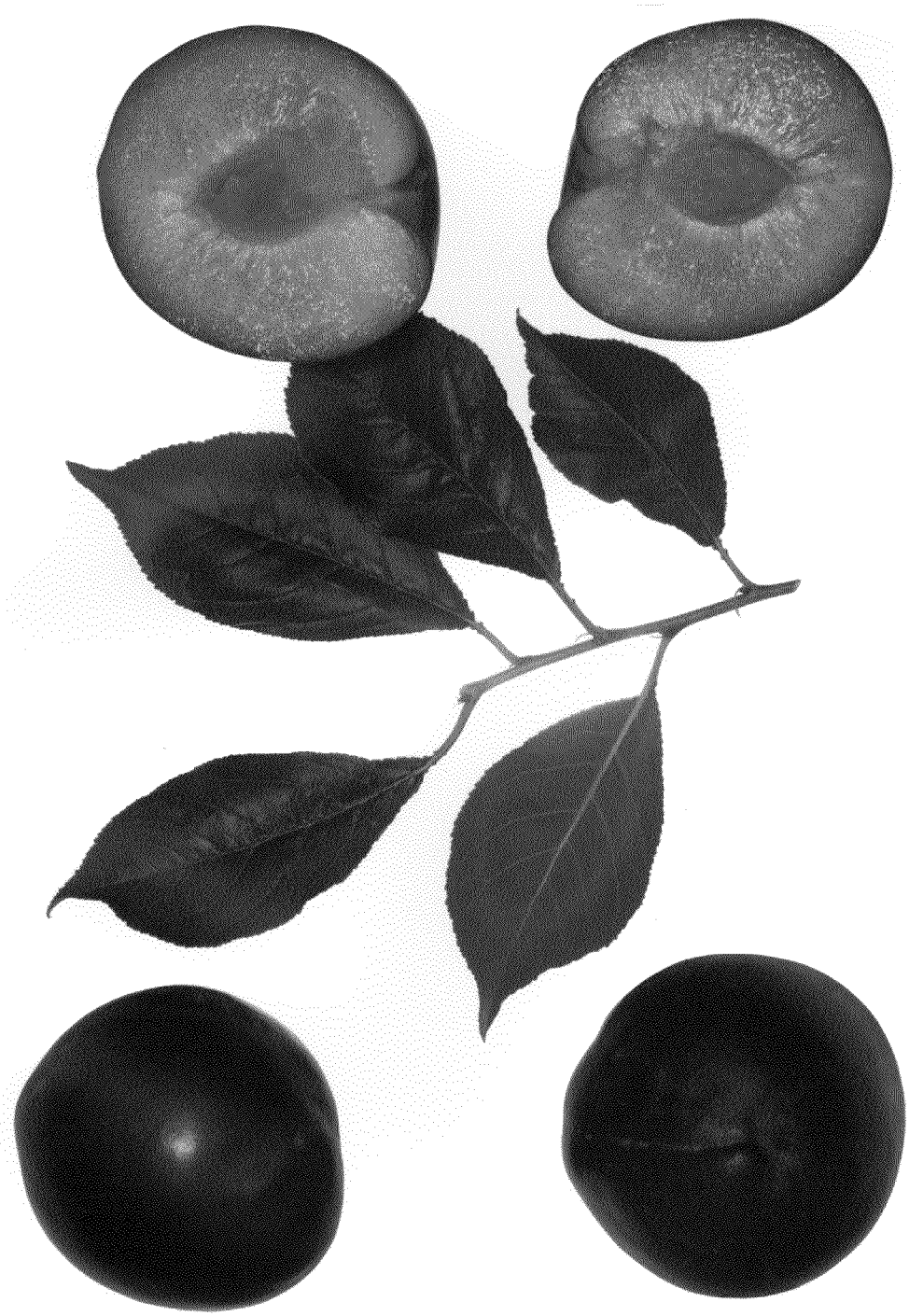

* * * * *